US010799387B2

(12) United States Patent
Brinker et al.

(10) Patent No.: US 10,799,387 B2
(45) Date of Patent: Oct. 13, 2020

(54) METHOD AND APPARATUS FOR REDUCING SNORING

(71) Applicant: BLR SleepWell LLC, Houston, TX (US)

(72) Inventors: Mark R. Brinker, Houston, TX (US); Jeffrey C. London, Houston, TX (US); Barry W. Raborn, Bellaire, TX (US)

(73) Assignee: BLR Sleepwell, LLC, Houston, TX (US)

(*) Notice: Subject to any disclaimer, the term of this patent is extended or adjusted under 35 U.S.C. 154(b) by 701 days.

(21) Appl. No.: 14/605,410

(22) Filed: Jan. 26, 2015

(65) Prior Publication Data

US 2016/0213507 A1 Jul. 28, 2016

(51) Int. Cl.
*A61F 5/56* (2006.01)

(52) U.S. Cl.
CPC ....................... *A61F 5/56* (2013.01)

(58) Field of Classification Search
CPC ........ A61F 13/02; A61F 13/12; A61F 13/126; A61F 13/128; A61F 13/14; A61F 13/141; A61F 13/143; A61F 13/146; A61F 13/148; A61F 5/56; A61F 5/566; A61F 5/08; A61F 5/40; A61F 2005/563; A61F 2007/0013; A61F 13/122–128; A61F 5/58; A61F 7/0013; A61F 7/0015; A61F 5/058; A61F 5/05825; A61F 5/05883; A61F 5/05891; A61F 5/37; A61F 5/3707; A61F 7/00; A61F 2007/0001–0003; A61F 2007/0015; Y10S 602/903; Y10S 602/902–904; A45D 44/22; A63B 23/025; A63B 23/03; A63B 23/18; A47D 27/38
USPC ...... 433/6, 7, 11, 19, 24; 128/848, 861, 857, 128/859, 862; 602/902, 52, 54; 606/201, 606/204, 204.15–204.55, 199; 604/304, 604/308
See application file for complete search history.

(56) References Cited

U.S. PATENT DOCUMENTS

| 2,397,648 | A | | 4/1946 | Butler |
|---|---|---|---|---|
| 5,690,121 | A | | 11/1997 | Miller |
| 5,752,524 | A | | 5/1998 | Corcoran |
| 5,829,441 | A | * | 11/1998 | Kidd ...................... A61F 5/566 |
| | | | | 128/848 |
| 6,512,159 | B1 | | 1/2003 | Shesol et al. |
| 7,032,598 | B2 | | 4/2006 | Portnoy |

(Continued)

FOREIGN PATENT DOCUMENTS

WO WO 94/20051 9/1994

OTHER PUBLICATIONS

Earth's Lab, Zygomatic Processes, Aug. 8, 2018, https://www.earthslab.com/anatomy/zygomatic-processes/.*

(Continued)

*Primary Examiner* — Keri J Nelson
*Assistant Examiner* — Michelle J Lee
(74) *Attorney, Agent, or Firm* — McAughan Deaver PLLC

(57) ABSTRACT

A mandible support device comprising a structural member comprising a support component and an adhesive component. The support component is configured to extend from the head or face above the mandible to the region of the gonial angle. The adhesive component is configured such that the structural member can be temporarily attached to the skin.

20 Claims, 4 Drawing Sheets

(56) References Cited

U.S. PATENT DOCUMENTS

| | | | |
|---|---|---|---|
| 7,793,661 B2* | 9/2010 | Macken | A61F 5/56 128/846 |
| 7,832,403 B2 | 11/2010 | Halstrom et al. | |
| 8,188,330 B2 | 5/2012 | Beaudry | |
| 8,585,617 B2 | 11/2013 | Mashiach et al. | |
| 8,613,283 B2 | 12/2013 | Hegde et al. | |
| 8,695,607 B2 | 4/2014 | Hohenhorst et al. | |
| 2003/0056785 A1* | 3/2003 | Narihiko | A61F 5/56 128/201.26 |
| 2003/0190339 A1 | 10/2003 | Skover et al. | |
| 2004/0089310 A1* | 5/2004 | Portnoy | A61F 5/56 128/848 |
| 2004/0153019 A1* | 8/2004 | Beaudry | A61F 5/08 602/42 |
| 2005/0133026 A1* | 6/2005 | Seleznev | A61F 5/56 128/200.24 |
| 2006/0106330 A1 | 5/2006 | Andrade et al. | |
| 2010/0294284 A1* | 11/2010 | Hohenhorst | A61F 5/012 128/848 |
| 2011/0265802 A1 | 11/2011 | Ha | |
| 2013/0220339 A1* | 8/2013 | Koike | A61F 5/56 128/848 |
| 2014/0000632 A1* | 1/2014 | Chen | A61F 5/56 128/848 |
| 2014/0048078 A1* | 2/2014 | Ahnblad | A61F 13/122 128/848 |
| 2014/0366889 A1* | 12/2014 | Riley | A61F 9/045 128/845 |
| 2016/0015154 A1* | 1/2016 | Veeder | A45D 44/22 606/204.35 |
| 2016/0184128 A1* | 6/2016 | Zweig | A61F 5/56 128/848 |

OTHER PUBLICATIONS

Earth's Lab, Zygomatic Processes, Aug. 8, 2018, https://www.earthslab.com/anatomy/zygomatic-processes/ (Year: 2018).*

Young, L., International Search Report for International Patent Application No. PCT/US15/64602, dated Feb. 23, 2016, United States Patent and Trademark Office.

Young, L., Written Opinion for International Patent Application No. PCT/US15/64602, dated Feb. 23, 2016, United States Patent and Trademark Office.

Senny, F., et al., "Mandible Behavior in Obstructive Sleep Apnea Patients Under CPAP Treatement", The Open Sleep Journal, 2012, vol. 5.

Thomas, S., International Search Report for International Patent Application No. PCT/US17/18168, dated Apr. 25, 2017, United States Patent and Trademark Office.

Thomas, S., Written Opinion for International Patent Application No. PCT/US17/18168, dated Apr. 25, 2017, United States Patent and Trademark Office.

Bai, L., International Preliminary Report on Patentability for International Patent Application No. PCT/US2015/064602, The International Bureau of WIPO, dated Aug. 10, 2017.

* cited by examiner

METHOD AND APPARATUS FOR REDUCING SNORING

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The inventions disclosed and taught herein relate generally to a device and method for reducing or eliminating snoring; and more specifically relate to a simple, comfortable, and easy to manufacture device for the reduction or elimination of snoring and a method for using the same.

Background Information and Description of the Related Art

The fundamental cause of snoring is a restriction or blocking of the air passage in the throat. Such a restriction in the throat air passage may occur during sleeping, when muscles of the face and throat relax. The relaxed muscles reduce support of the mandible, which allows the mandible to shift in a posterior direction. In turn, the shifted mandible allows soft tissue in the back of the throat to sag. The sagging soft tissue then blocks the flow of air needed for breathing.

A sleeping person will generally respond to the blockage of the airway by breathing harder, thereby increasing the air pressure in the airway. The increased air pressure results in a partial opening of the airway. The snoring sound is the restricted airflow vibrating the soft tissue. The snoring noise disturbs the sleep of others in the proximity of the snoring person, and the snoring person has laborious breathing that reduces the quality of sleep. Extreme cases of air passage blockage often result in a medical condition, called obstructive sleep apnea, where the quality of sleep is severely degraded and other deleterious health effects are exhibited.

There are a number of types of treatments for snoring in the prior art. These various treatments can be divided into at least two classes: surgical and mechanical. Surgical treatments include palatal implants, in which braided strands of polyester filament are injected into the snorer's soft palate, with the intention of stiffening the soft tissues and reducing snoring. Another surgical treatment is uvulopalatopharyngoplasty, which can be conducted using traditional or laser-assisted surgical techniques to shorten the soft palate and remove the snorer's uvula, enlarging the airway with the intent of reducing vibration of the soft tissues during sleep. Another surgical treatment is radiofrequency tissue ablation (somnoplasty), in which low-intensity radiofrequency signals are used to shrink tissue in the soft palate. The surgical treatments for snoring all have the risks associated with surgery, are expensive, and of uncertain effectiveness.

Mechanical treatments for snoring include continuous positive airway pressure (CPAP) devices. The user of a CPAP device wears a mask over the nose and/or mouth while sleeping. The mask is attached to an air pump that forces air through the snorer's airway to raise the air pressure inside the airway to approximately 70 to 120 Pascal above atmospheric pressure. The increased pressure functions to reduce or eliminate the airway blockage caused by the sagging soft tissue. The CPAP is generally considered to be the most reliable treatment for snoring and obstructive sleep apnea. However, the equipment is bulky and many individuals who begin using a CPAP find it uncomfortable or disruptive to sleep. Studies suggest that approximately half of the individuals who begin using a CPAP machine to treat sleep apnea cannot tolerate them and discontinue their use.

Other mechanical treatments for snoring include oral appliances. Oral appliances are form fitting dental mouthpieces that help advance the position of the tongue and soft palate with the intent of opening the airway, often by repositioning the lower mandible to jut forward into an unnatural position. Oral appliances are relatively expensive, and have a variety of sometimes-severe side effects, including jaw pain, facial discomfort, and modified tooth alignment.

Examples of such oral appliances include U.S. Pat. No. 7,832,403 issued to Halstrom on Nov. 16, 2010, in which a mandible position device is described as having a maxillary dentition engagement component and a mandibular dentition engagement component, each on opposite sides of a plane extending therebetween. An adjustable connection couples the maxillary dentition engagement component with the mandibular dentition engagement component. The adjustable connection has a first adjustment screw having a longitudinal axis perpendicular to the plane. The first and second adjustable screws are independently adjustable and structures to effect horizontal and vertical displacement, respectively, of the maxillary dentition engagement component relative to the mandibular dentition engagement component.

Other examples of such oral appliances include U.S. Pat. No. 8,613,283 issued to Hegde on Dec. 24, 2013, in which a mandibular advancement appliance is described which is secured to a subject's dentition. The appliance may adjust a portion of the subject's lower dentition relative to the upper dentition while maintaining a distance between the upper and lower dentition. The appliance may also allow for the free rotation of the lower dentition relative to the upper dentition for increased comfort. Additionally, the appliance may also be utilized with a tongue retention assembly for maintaining a position of the subject's tongue relative to the device for treating sleep disordered breathing.

A third category of mechanical devices for the reduction or prevention of snoring includes devices that are worn externally on or about the face and/or neck of the subject. Some such devices are braces and similar structures that are worn about the head and neck. For example, U.S. Pat. No. 8,695,607 issued to Hohenhorst on Apr. 15, 2014, discloses apparatus, systems, and methods to constrain and/or support tissue structures along an airway. Hohenhorst discloses apparatus, systems, and methods that externally brace tissues structures in, on, or near the neck, along the walls of the pharyngeal airway itself. The apparatus, systems, and methods mechanically support these tissue structures in, on, or near the neck in a desired orientation, biased away from the pharyngeal airway. The mechanical support that the apparatus, systems, and methods provide affirmatively resists collapse of the tissue structures in, on, or near the neck toward and into the pharyngeal airway, thereby moderating or preventing the incidence of sleep apnea. Such apparatus, systems, and methods disclosed by Hohenhorst include, for example, a full collar structure that is worn about the entire neck at the level of the larynx and including releasable fasteners so that an individual can adjust the fit and form of the collar around their neck.

Other such devices are intended to adhere to the face or neck of a subject to mechanically enlarge an airway. For example, U.S. Pat. No. 5,752,524 issued to Corcoran on May 19, 1998, discloses a device for preventing or reducing snoring. The Corcoran device includes in combination a rigid ellipsoidal support base having a concave interior surface and a convex exterior surface and an adhesive material for attaching to human epidermis layered on a predominance of the entire convex interior surface. The device is stated to be "particularly useful to prevent snoring in a sleeping human by providing a small air passage between the superior maxillary facial muscles of the face, and the superior maxilla (upper jaw bone), which allows for the intake and output of air such that the sleeping individual does not have to intake and output air through the nose. By this means, snoring is prevented, or markedly reduced."

Another example of such a device is disclosed in U.S. Pat. No. 7,793,661 issued to Macken on Sep. 14, 2010. Macken discloses an anti-snoring device that attaches to a specific area of the neck. The attachment means can be an adhesive, a clip or an implant. The device exerts a predetermined pulling force on this area of the neck, causing this area of the neck to expand outward from its normal position. This expansion opens a blockage in the throat of a sleeping person, thereby eliminating snoring and helping some people with obstructive sleep apnea.

Another example of such a device is disclosed in U.S. Pat. No. 8,188,330 issued to Beaudry on May 29, 2012. Beaudry discloses a dressing mechanism comprising a first section, a second section, and a third section. The first section and the third section each may include one side having an adhesive layer. An overlaying, non-adhesive barrier layer may be located between a portion of the adhesive layer and a first or third section. At least one of the first or third sections may further include a plurality of hook or loop members which are arranged to be fastened to corresponding hook or loop members of a hook and loop fastener. Several forms of the mechanism disclosed by Beaudry related to epidermal lifting mechanisms and methods for increasing the flow of gases into the human body and more specifically to an epidermal lifting mechanism and method for allowing more oxygen to pass through the nasal cavity thus increasing both the flow of oxygen into the lungs and the flow of air exhaled from the lungs.

The inventions disclosed and taught herein are directed to a device and method for reducing or preventing snoring that is not present in the prior art. The inventions disclosed and taught herein are simple and comfortable to use, inexpensive to manufacture, and do not require surgical intervention.

BRIEF SUMMARY OF THE INVENTION

In brief summary, one possible embodiment of the disclosed invention the mandible support device comprises a structural member having a first side and a second side and comprising a first section, a second section, and a third section. The first section and the third section of the structural member each comprise a proximal portion and a distal portion; where the proximal portion of the first section is coupled to the second section, the proximal portion of the third section is coupled to the second section, and the second section is shaped and sized to correspond substantially to the shape of gonial angle, also referred to as the angle of the mandible. At least a portion of at least one of the first section, the second section, and the third section may be comprised of a material exhibiting at least some elastic properties. The adhesive component comprises a first adhesive layer and a second adhesive layer, each comprising a first adhesive side and a second side, where the second side of the first adhesive layer is disposed on at least a portion of the first side of the distal portion of the first section and the second side of the second adhesive layer is disposed on a least a portion of the first side of the distal portion of the third section. The structural member is shaped and sized to extend at least from the region above the mandible, for example the zygomatic bone and/or maxilla, to the region on, behind or beneath the gonial angle, and along the course of the mandible towards the chin.

In brief summary of another of many embodiments of the invention, is a mandible support device comprising a structural member. The structural member comprises a support component and an adhesive component, wherein the support component is configured to extend from at least a portion of a zygomatic bone and/or maxilla of a face to at least a portion of the gonial angle and the adhesive component is configured such that the structural member can be temporarily attached to the epidermis. The function of the mandible support device is to provide passive support of the mandible to reduce the posterior movement of the mandible during sleep. One end of the support component is adhered to the epidermis of the head or face above the mandible, for example, about the zygomatic bone and/or maxilla. Another end of the mandible support device is adhered to the epidermis on, beneath, or behind the gonial angle. Tension applied to the support component restricts posterior movement of the mandible that naturally occurs as a result of gravity and muscle relaxation.

The invention also relates to a method for using the mandible support device described herein, where the first side of the distal portion of the first section of the structural member is affixed to the epidermis covering the zygomatic bone and/or maxilla, the second section of the structural member is positioned on, behind, or beneath the gonial angle and the first side of the distal portion of the third section of the structural member is affixed to the epidermis of the region along the course of the mandible toward the chin.

DETAILED DESCRIPTION OF THE INVENTION

Figure 1:
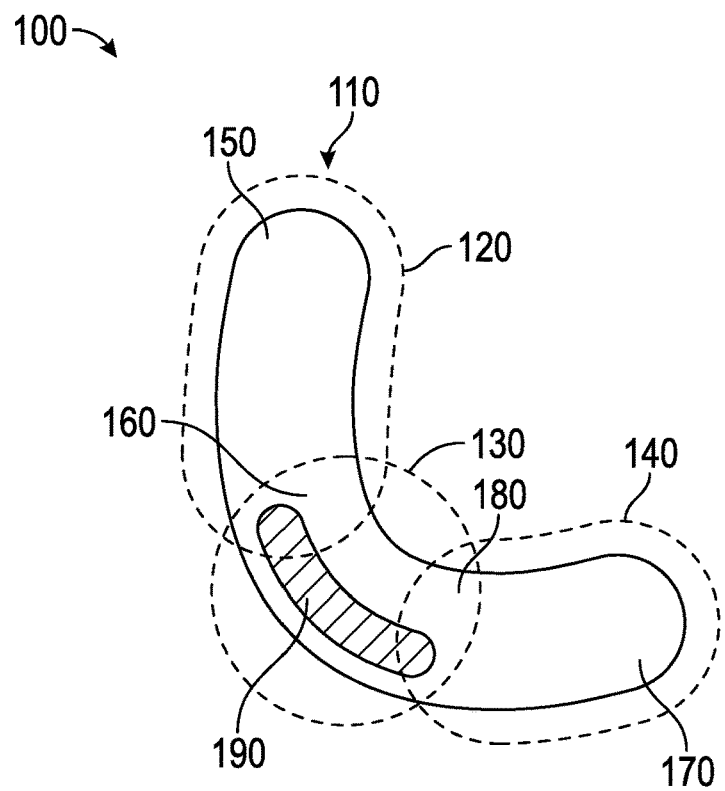
FIG. 1 illustrates a top plan view of a mandible support device according to an embodiment of the invention.

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Applicants have created a mandible support device designed to be used during sleep for the prevention or reduction of snoring. The mandible support devise comprises a flexible strap, wherein said strap is sized to extend at least from the region above the mandible, for example the zygomatic bone and/or maxilla, the region on, behind or beneath the gonial angle. The structural member also comprises an adhesive material, wherein the adhesive material is applied to the structural member such that the structural member can be temporarily attached to the epidermis covering the face and/or neck of a human.

In one of many possible embodiments of the present invention, the mandible support device comprises a structural member. The structural member in turn comprises a support component and an adhesive component, wherein the support component is configured to extend from at least a portion of the region above the mandible, for example the zygomatic bone and/or maxilla, to at least a portion of the region of the gonial angle, and the adhesive component is configured such that the structural member can be temporarily attached to epidermis. The function of the mandible support device is to provide passive support of the mandible to reduce or restrict the posterior movement of the mandible that naturally occurs during sleep. The support component is adhered to the epidermis at least on or about the region above the mandible, such as the zygomatic bone and/or the maxilla, and the gonial angle. Tension in the support component restricts posterior movement of the mandible that naturally occurs as a result of gravity and muscle relaxation.

FIG. 1 shows an alternative embodiment of the present invention. The mandible support device 100 comprising a structural member 110. The structural member 110 has a first side and a second side, and further comprises a first section 120, a second section 130, and a third section 140. The first section 120 comprises a first section distal portion 150 and a first section proximal portion 160. The third section 140 comprises a third section distal portion 170 and a third section proximal portion 180. The first section proximal portion is coupled to the second section 130 and the third section proximal portion 180 is coupled to the second section 130. The second section 130 is shaped and sized to correspond substantially to the shape and size of the gonial angle. The shape and size of the second section 130 may be configured to be somewhat larger or smaller than the gonial angle of a particular user or of average gonial angle size and shape, depending on the specific application and the intended positioning of the first section 120 relative to the user's zygomatic bone, maxilla, or other region above the mandible. The third section is configured to run from the region of the gonial angle along the mandible toward the chin.

The structural member 110 has a support component and an adhesive component, with a suitable adhesive as previously discussed herein. The adhesive component of the structural member 110 results from an adhesive layer disposed to the first side of the structural member 110. The adhesive component should include an adhesive layer disposed on at least the regions of the first section distal end 150 and the third section distal end 170. However, an adhesive layer can be applied to the second section 130 in addition, creating a third adhesive portion in the second section 130. In addition, an adhesive layer can be applied to the entire first side of the structural member 110, thereby creating an adhesive region over the entirety of the first side of the structural member 110. The amount, type, quantity and placement of the adhesive and adhesive regions may be adjusted as appropriate, as would be understood by a person of skill in the art to achieve the function of the mandible support device 100.

The mandible support device 100 can also include a positioning component 190. Positioning component 190 is disposed substantially within the second section 130 and is configured to substantially match the shape and size of the gonial angle. Positioning component 190 can be disposed on the first side or the second side of the support component of the structural member 110. As discussed above, the positioning component 190 serves two primary functions: first, to assist in the correct placement of the mandible support device 100, and second, to provide additional support of the mandible, thereby preventing posterior movement of the mandible.

A positioning component 190 can be used to aid in the positioning of the second section 130 of the structural member 110 to the region on, behind, or beneath the gonial angle. The positioning component 190 should be disposed on the structural member 110 in such a manner that the location of the contours of the positioning component 190 can be felt relative to the gonial angle when the structural member 110 is applied on the user. The positioning component 190 should be sufficiently flexible to be comfortable on the user's epidermis and to be able to conform to the shape and size of the region on, beneath, or behind the gonial angle. The positioning component 190 should also be sufficiently rigid to provide some tactile resistance, thus providing tactile feedback to the user regarding placement of the second section 130 of the structural member 110 relative to the gonial angle.

The positioning component 190 has an additional function of providing support to the mandible and reducing a shift of the mandible in a posterior direction. Specifically, and as discussed previously, the positioning component 190 when adhered to the epidermis covering the face and neck on, beneath, or behind the gonial angle provides a ledge-like structure against which the gonial angle can rest upon relaxation of the facial and neck muscles, thereby aiding in the prevention of a posterior shift of the mandible.

The mechanism of operation of the mandible support device 100 is dependent on passive external support of the mandible. This passive support is provided at the gonial angle. During sleeping, the muscles of the face and throat relax. During a waking state, these muscles provide support for the mandible; relaxation of the muscles during sleep results in a reduction of support of the mandible. The reduced muscular support allows the mandible to shift in a posterior direction with the force of gravity. In turn, the shifted mandible allows soft tissue in the back of the throat to sag. The sagging soft tissue blocks the flow of air needed for breathing.

Such a restriction in the throat air passage may occur during sleeping, when muscles of the face and throat relax. The relaxed muscles reduce support of the mandible, which allows the mandible to shift in a posterior direction. In turn, the shifted mandible allows soft tissue in the back of the throat to sag. The sagging soft tissue then blocks the flow of air needed for breathing. A sleeping person will generally respond to the blockage of the airway by breathing harder, thereby increasing the air pressure in the airway. The increased air pressure results in a partial opening of the airway. The snoring sound is the restricted airflow vibrating the soft tissue.

The amount of support provided by various mandible support devices 100 can also be affected by the material comprising the support component of the structural member 110. The support component of the structural member 110 can comprise any suitable material, including but not limited to paper and paper-like material, woven natural fiber, woven synthetic fiber, and woven blended fiber. The support component of the structural member 110 can include elastic materials, either in lateral sections of the structural member or as fibers woven into the material of the support component of the structural member 110. The elasticity, or lack thereof, of the support component of the structural member can therefore be controlled by choice of material used to construct the support component of the structural member 110 as well as by modifying sectional construction materials of the support component of the structural member 110. Increasing elasticity of the material will tend to decrease with amount of support the mandible support device 100 can provide to prevent posterior movement of the mandible during sleep. However, increasing the elasticity of the material used for the support component of the structural member 110 will tend to increase the physical comfort of the mandible support device 100 for the user. Ideally, the elasticity of the material will allow sufficient force to provide adequate support for the mandible, while still allowing the user to move his or her mandible for, e.g., talking while awake. The degree of support provided by an at least partially elastic mandible support device 100 can also be adjusted by the user during application of the mandible support device 100 by the degree to which the structural member 110 is stretched between the region of epidermis on, behind or beneath the gonial angle to the region about the zygomatic bone.

Figure 2:
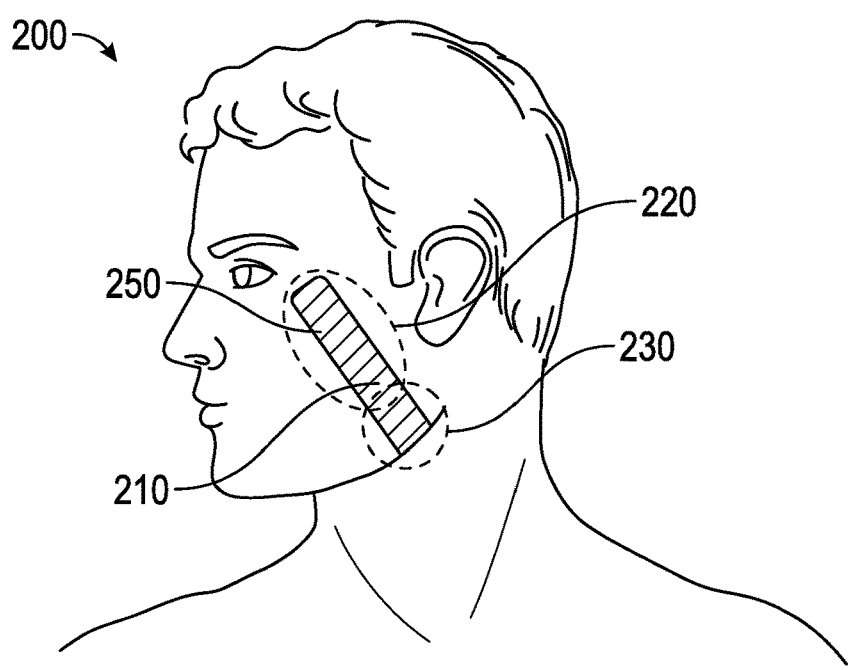
FIG. 2 illustrates a side view of a subject wearing a mandible support device according to an embodiment of the invention.

Turning to FIG. 2, one possible location of application of the mandible support device 200 is depicted. Mandible support device 200 comprises a structural member 210 that comprises a support component and an adhesive component. The first section 220 of the structural member 210 has been adhered to the soft tissue above the mandible, such as the epidermis about the zygomatic bone and/or maxilla, by use of the adhesive component of the structural member 210. The second section 230 of the structural member 210 is situated on, beneath, or behind the gonial angle. In the embodiment depicted in FIG. 2, the first section 220 of the structural member 210 contains an adhesive component disposed to the first side of the structural member 210 in at least a portion of the first section 210. The second section 230 of the structural member 210 may or may not have an adhesive component disposed on it, depending on the specific application as would be understood be a person of skill in the art.

Figure 3:
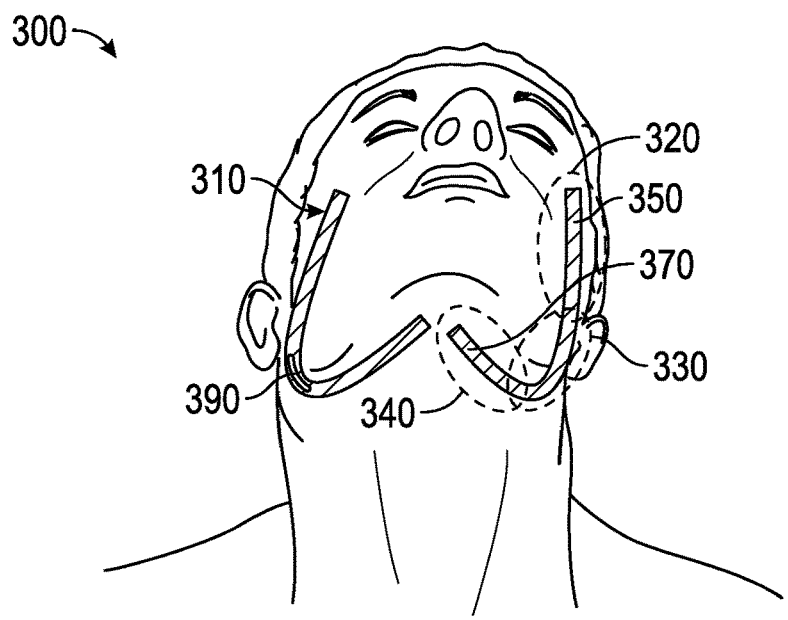
FIG. 3 illustrates an alternative side view of a subject wearing a mandible support device according to an embodiment of the invention.

FIG. 3 depicts a perspective view of the placement of two mandible support devices 300 applied to a user. The structural member 310 of the mandible support device 300 is affixed to the user's face and neck. The distal end 350 of the first section 320 of the structural member 310 is affixed temporarily to the epidermis about the zygomatic bone and/or maxilla of the user, taking advantage of the adhesive component of the structural member 310. The second section 330 of the structural member 310 is disposed about the region on, beneath, or behind the gonial angle. The second section 330 of the structural member 310 may be temporarily affixed to the epidermis of the region on, behind or beneath the gonial angle using an adhesive component of the structural member 310. However, affixing of the second section 330 of the structural member 310 to the epidermis of the region posterior to the gonial angle is not a necessary aspect of the present invention. The distal end 370 of the third section 340 of the structural member 310 is affixed to the epidermis of a portion of the neck running substantially parallel to or along the mandible toward the chin by way of an adhesive component of the structural member 310. If the structural member 310 contains a positioning component 390, the positioning component 390 is situated at the region on, behind, or beneath the gonial angle.

The function of the mandible support device 300 is to provide passive support to the mandible at the gonial angle to prevent or reduce or restrict a posterior shift of the mandible during sleep when the muscles of the face and the neck are relaxed. The adhesive component of the structural member 310 anchors the support component of the structural member 310 on the soft tissue of the face or head above the mandible and the region under and/or posterior to the chin. The placement of the adhesive component of the distal end 350 of the first section 320 of the structural member 310 may be preferentially, though not necessarily, located on or about the zygomatic bone or the maxilla. The weight of the mandible is thereby supported by the first section 320 of the support component of the structural member 310. The third section 340 of the structural member 310 stabilizes the position of the second section 330 of the structural member 310, allowing the curve of the second section 330 of the structural member 310 to cradle the gonial angle, supporting the mandible and restricting its shift in a posterior direction.

One method of use of the mandible support device 300 to the face of the user begins with the application of the distal end 350 of the first section 320 to the epidermis about the region of zygomatic bone or the maxilla, using the adhesive component that is disposed on the one side of the support component of the structural member 310. If the mandible support device 300 has a positioning component 390, the positioning component 390 should be positioned on, behind, or beneath the gonial angle, such that the curve of the positioning component 390 approximates the gonial angle. If no positioning component 390 is present on the structural member 310, the second section 330 of the structural member 310 should be placed sufficiently on, behind, or beneath the gonial angle so that the structural member 310 can provide resistance against posterior movement of the mandible. Tension should be applied to the structural member 310 when bringing to the region on, behind, or beneath the gonial angle. If the second section 330 of the structural member 310 is equipped with an adhesive component, tension should be maintained in the first section 320 of the structural member 310 while the adhesive component of the second section 330 is affixed to the epidermis on, behind, or beneath the gonial angle. If the second section 330 of the structural member 310 is not equipped with an adhesive component, tension in the first section 320 and the second section 330 of the structural member 310 should be maintained as the structural member is positioned around the region on, behind or beneath the gonial angle and until the distal end 370 of the third section 340 of the structural member 310 is affixed to the epidermis of the neck along the course of the mandible toward the chin. In this method of use of the mandible support device 300, the distal end 350 of the first section 320 of the structural member 310 is pulled toward the gonial angle and adhered to the epidermis covering the area about the region under or posterior to the chin using the adhesive component that is disposed on one side of the support component of the distal end 370 of the third section 340 of structural member 310. It should be noted, of course, that the method of application could also be reversed, so that the distal end 370 of the third section 340 of the structural member 310 is adhered first to the epidermis about the region under or behind the chin, and the structural member is pulled in the posterior direction around the gonial angle and upward toward the region about the zygomatic bone and/or maxilla. Likewise, the second section 330 could be held against the epidermis on, behind, or beneath the gonial angle while the first section 320 and the third section 340 are pulled toward the zygomatic bone and the region under the chin, respectively, and affixed with the adhesive component of the structural member 310 to their appropriate positions as described herein. In any instance, the force with which the structural member 310 is pulled behind or beneath the gonial angle will affect the amount of support provided to the mandible. The degree of support provided can therefore be altered depending on the needs of the user, where a greater amount of support can be provided for users that experience a higher degree of posterior mandibular movement during sleep.

In an alternative embodiment based on FIG. 3, the third section 340 may be substantially elongated beyond what is depicted in FIG. 3 such that it is configured to cross under the chin to the opposite side of the face and be adhered to the epidermis about the opposite zygomatic bone or maxilla. Such a configuration would provide an altered degree of support to the mandible.

Figure 4:
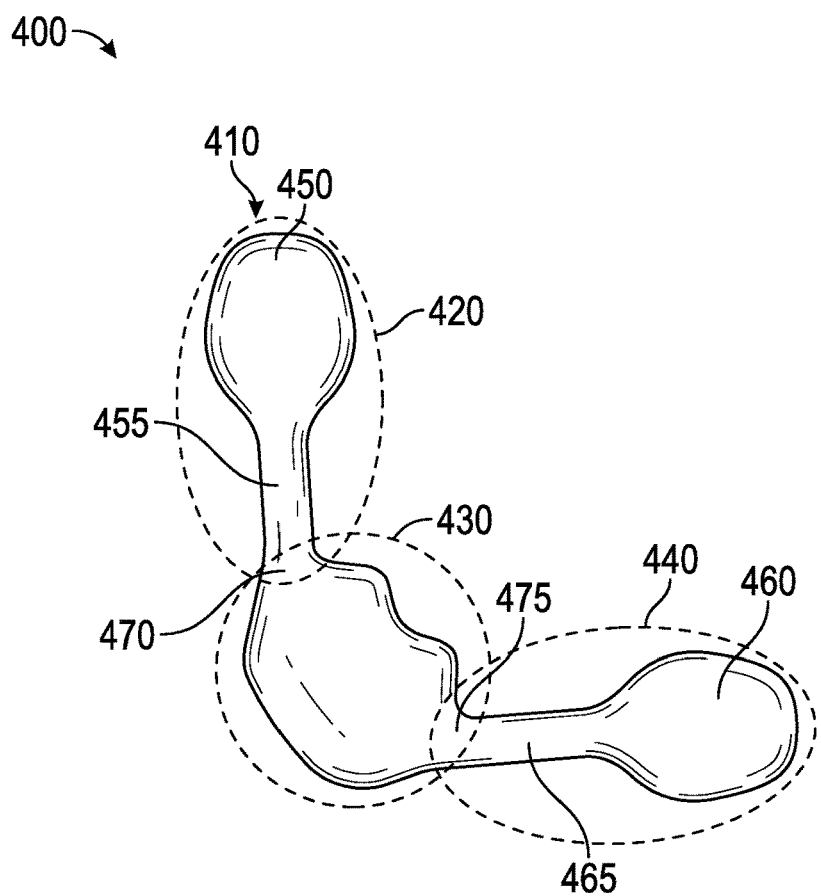
FIG. 4 illustrates a top plan view of a mandible support device according to an embodiment of the invention.

FIG. 4 shows an alternative embodiment of the mandible support device 400 comprising a structural member 410. The structural member 410 has a first side and a second side, and further comprises a first section 420, a second section 430, and a third section 440. The first section 420 comprises a first section distal portion 450 and a first section proximal portion 470. The third section 440 comprises a third section distal portion 460 and a third section proximal portion 475. The first section proximal portion 470 is coupled to the second section 430 and the third section proximal portion 475 is coupled to the second section 430. The second section 430 is shaped and sized to correspond substantially to the shape and size of the gonial angle. The portions of the structural member 410 that span between the distal ends, 450, 460, and their respective proximal ends, 470, 475, can be dimensioned to different width, material, and/or elasticity depending on the specific application technique desired.

Figure 5:
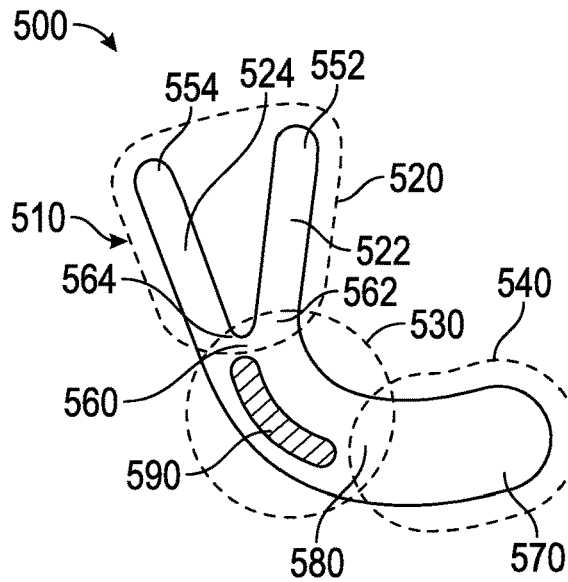
FIG. 5 illustrates a top plan view of a mandible support device according to an embodiment of the invention.

FIG. 5 shows an alternate embodiment of the mandible support device 500. comprising a structural member 510. The structural member 510 has a first side and a second side, and further comprises a first section 520, a second section 530, and a third section 540. The first section 520 comprises two branches, an anterior branch 522 and a posterior branch 524. The anterior branch 522 and the posterior branch 524 are each comprised of a distal portion 552 and 554, respectively, and a proximal portion 562 and 564, respectively. As indicated in FIG. 5, the anterior branch proximal portion 562 and the anterior branch proximal portion 564 are coupled at the point where the first section 520 is coupled to the second section 530. The third section 540 comprises a third section distal portion 570 and a third section proximal portion 580. The first section proximal portion 560 is coupled to the second section 530 and the third section proximal portion 580 is coupled to the second section 530. The second section 530 is shaped and sized to correspond substantially to the shape and size of the gonial angle. Application of this embodiment of mandible support device 500 on the face of the user would include the application of both the first section anterior branch 522 and the first section posterior branch 524 to the soft tissue of the face above the mandible. For instance, in one possible application, the first section anterior branch 522 would be adhered to the epidermis in the region of the zygomatic bone, while the first section posterior branch 524 would be adhered to the epidermis in the region of the maxilla. The mandible support device 500 may include positioning component 590.

Figure 6:
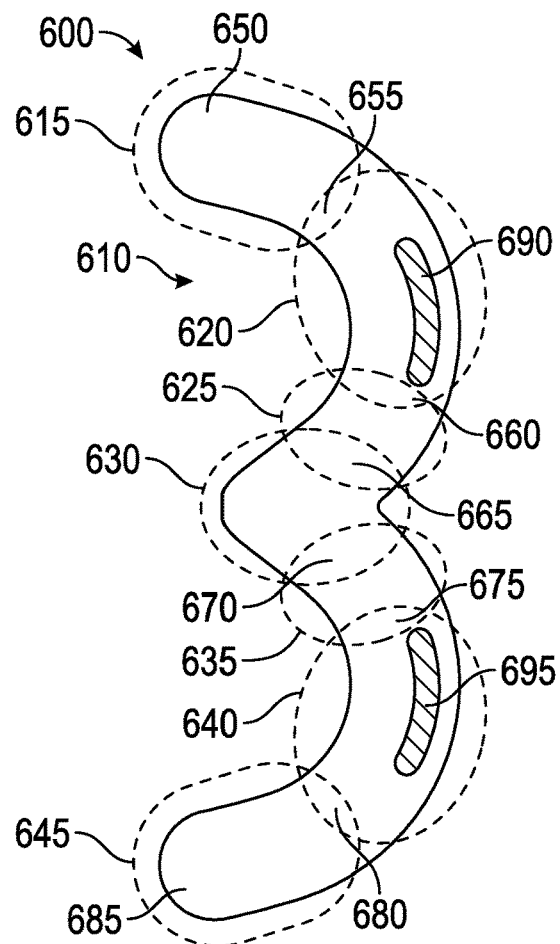
FIG. 6 illustrates a top plan view of a mandible support device according to an embodiment of the invention.

FIG. 6 depicts an alternative embodiment of the invention, in which the mandible support device 600 is configured to span the distance from the region of the zygomatic bone or maxilla of one side of the face to the region of the zygomatic bone or maxilla of the second side of the face, passing on, behind, or beneath the gonial angle of the first side and the second side of the face. In this embodiment, the structural member 610 comprises a support component and an adhesive component. The support component of the structural member 610 comprises a first side and a second side. The support component of the structural member 610 comprises a first section 615, a second section 620, a third section 625, a fourth section 630, a fifth section 635, a sixth section 640 and a seventh section 645. The first section 615 comprises a distal region 650 and a proximal region 655. The third section 625 comprises a proximal region 660 and a distal region 665. The fifth section 635 comprises a distal region 670 and a proximal region 675. The seventh section 645 comprises a proximal region 680 and a distal region 685.

The proximal end 655 of the first section 615 is coupled to the second section 620 and the proximal end of the third section 625 is coupled to the second section 620. The proximal end 680 of the seventh section 645 and the proximal end 675 of the fifth section 635 is coupled to the sixth section 640. The distal end 665 of the third section 625 and the distal end 670 of the fifth section 635 are coupled to the fourth section 630.

The second section 620 and the sixth section 640 of the support component of the structural member 610 are configured to correspond substantially to the shape and size of the gonial angle. The mandible support device 600 may include positioning components 690 and 695. Each of positioning components 690 and 695 are disposed substantially within second section 620 and sixth section 640, respectively. As with the embodiments described above, positioning components 690 and 695 may be disposed on the first side or the second side of the support component of the structural member 610. Also as discussed with regard to the other example embodiments disclosed herein, the support components 690 and 695 serve two principal functions: first, to assist in the correct placement of the mandible support device 600; and second, to provide additional support of the mandible, thereby preventing posterior movement of the mandible.

The proximal regions of the first section 615 and the third section 625 may be coincident at least to some extent with portions of the second section 620, as exemplified in the embodiment depicted in FIG. 6. Similarly, the proximal regions of the fifth section 635 and the seventh section 685 may be coincident with portions of the sixth section 640, as exemplified in the embodiment illustrated in FIG. 6. The distal regions of the third section 625 and the fifth section 635 are disposed about or otherwise linked to portions of the fourth section 630.

The structural member 610 also comprises an adhesive component, with a suitable adhesive as previously discussed herein. As with other exemplary embodiments discussed herein, the adhesive component of the structural member 610 results from an adhesive layer disposed to the first side of the structural member 610. The adhesive component should include an adhesive layer disposed on at least a portion of the distal region 650 of the first section 615, the distal region 685 of the seventh section 645, and either a portion of the fourth section 630 or a portion of the third section 625 and the fifth section 635. As previously described with regard to other exemplary embodiments disclosed herein, an adhesive layer can be applied to the entire first side of the structural member 610, thereby creating an adhesive region over the entirety of the first side of the structural member 610. The amount, type, quantity and placement of the adhesive and adhesive layers may be adjusted as appropriate, as would be understood by a person of skill in the art to achieve the function of the mandible support device 600.

The positioning components 690 and 695 may be used to aid in the positioning of the mandible support device 600 on the face and neck of the user. The positioning components 690 and 695 should be disposed on the structural member 610 in such a manner that the location of the contours of the positioning components 690 and 695 can be felt relative to the gonial angle when the structural member 610 is applied on the user. The positioning components 690 and 695 should be sufficiently flexible, as previously discussed, to be comfortable on the user's epidermis and to be able to conform to the shape and size of the region on, behind or beneath the gonial angle. The positioning components 690 and 695 should also be sufficiently rigid to provide some tactile resistance, thus providing tactile feedback to the user (or other individual applying the mandible support device 600 to the user) regarding the placement of the structural member 610 relative to the gonial angle.

Figure 7:
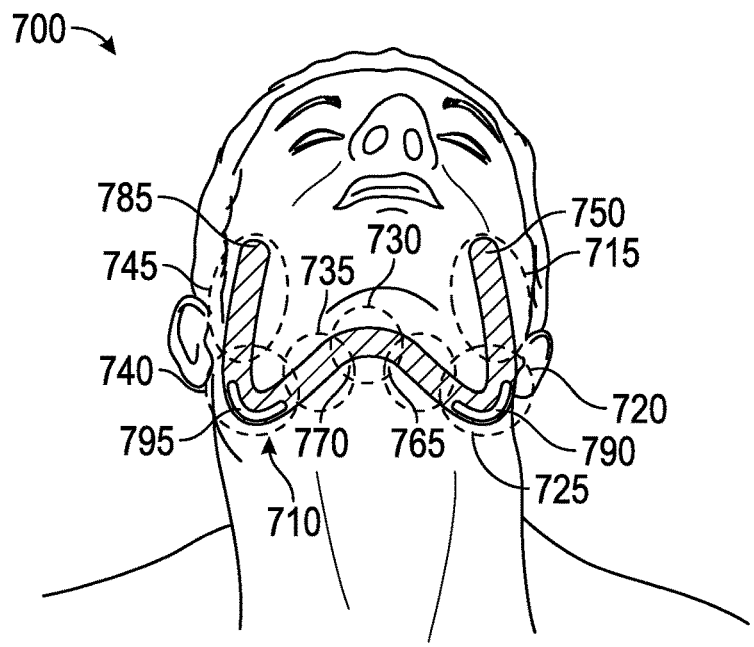
FIG. 7 illustrates a side view of a subject wearing a mandible support device according to an embodiment of the invention.

FIG. 7 depicts a perspective view of the placement of a mandible support device 700 according to one possible embodiment as applied to a user. The structural member 710 of the mandible support device 700 is affixed to the user's face and neck. The distal end 750 of the first section 715 of the structural member 710 is affixed temporarily to the epidermis about the zygomatic bone and/or maxilla of the user, taking advantage of the adhesive component of the structural member 710. The second section 720 of the structural member 710 is disposed about the region on, behind or beneath the gonial angle. The second section 720 of the structural member 710 may be temporarily affixed to the epidermis of the region on, beneath, or behind the gonial angle using an adhesive component of the structural member 710. However, affixing of the second section 720 of the structural member 710 to the epidermis of the region on, beneath, or behind the gonial angle is not a necessary aspect of the present invention. The distal end 765 of the third section 725 and the distal end 770 of the fifth section 735, and/or the fourth section 730, of the structural member 710 are affixed to the epidermis covering the neck in the region posterior to the chin by way of an adhesive component of the structural member 710. The distal end 785 of the seventh section 745 of the structural member 710 is affixed to the region of the zygomatic bone and/or maxilla of the user, in such an orientation that the sixth section 740 is disposed about the region on, behind, or beneath the gonial angle. If the structural member 710 contains positioning components 790, 795, the positioning components 790, 795 are situated at the region on, beneath, or behind the gonial angle. The method of application of the embodiment depicted in FIGS. 6 and 7 to a user would be similar to the method of application of other embodiments disclosed herein.

Figure 8:
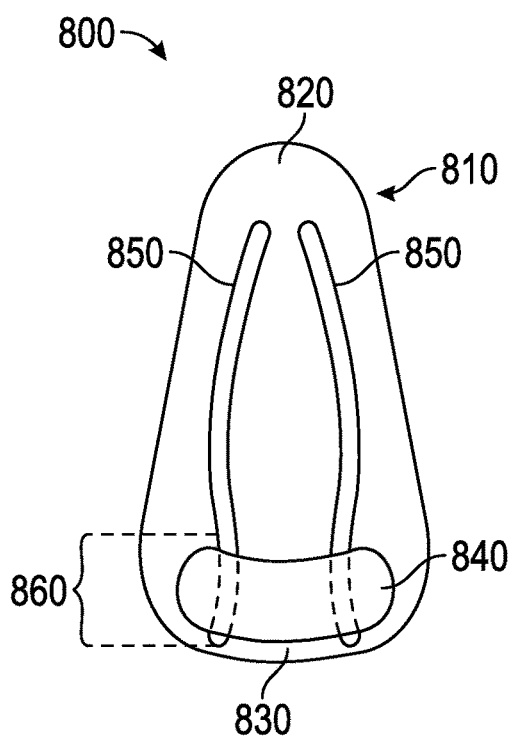
FIG. 8 illustrates a top plan view of a mandible support device according to an embodiment of the invention.

FIG. 8 is an illustration of one embodiment of the present invention. In this embodiment, mandible support device 800 is depicted as comprising structural member 810 having a first side and a second side and having a first end 820 and a second end 830. The structural member 810 may optionally include a positioning component 840 that may be shaped to approximate the shape and size of the gonial angle. The structural member 810 contains a support component and an adhesive component. The adhesive component is disposed on at least portions of one side of the support component, substantially near the first end and substantially near the second end. In the current embodiment, it is contemplated that the positioning component 840 would be optimally located on the side of the support component on which the adhesive component is disposed. However, it should be noted that the positioning component 840 can be located on either side of the support component, or internally to the support component, near the second end of the structural member if the structural member is thin enough to permit the edges of the positioning component 840 to be discerned by touch for purposes of placement on, beneath, or behind the gonial angle.

It is contemplated that the adhesive component of the present invention can be any appropriate adhesive known to person of skill in the art, where such adhesive is suitable for use on human skin for temporary adhesion of the support component to the epidermis. In this context, the term "temporary adhesion" is intended to refer to adhesion for a period of time sufficient to span at least 8 to 12 hours, and is removable by the user with minimal discomfort. Such adhesive is contemplated to be a self-adhesive material, an adhesive that must be wetted to exhibit adhesive properties, or any other suitable adhesive known in the art.

Figure 9:
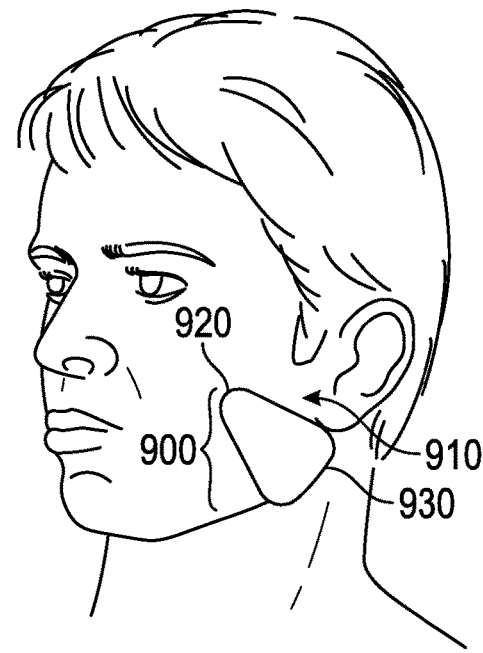
FIG. 9 illustrates a perspective view of a subject wearing a mandible support device according to an embodiment of the invention.

FIG. 9 illustrates the placement of the mandible support device 900 on a user. The first end 920 of the structural member 910 is adhered to the epidermis covering or near the zygomatic bone and/or the maxilla of the user. The second end 930 of the structural member 910 is adhered to the epidermis in the region posterior to the gonial angle of the user.

Figure 10:
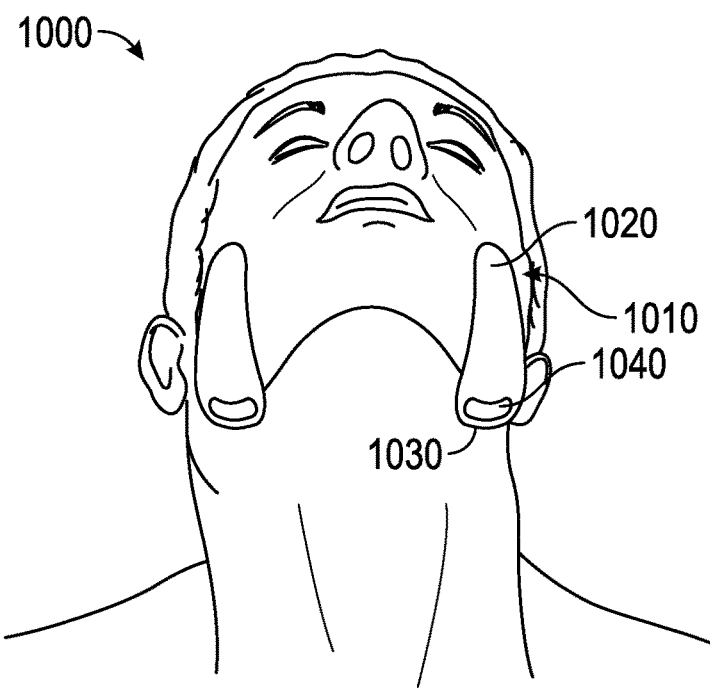
FIG. 10 illustrates a side view of a subject wearing a mandible support device according to an embodiment of the invention.

FIG. 10 shows an alternate view of the placement of the mandible support device 1000 on the user. In FIG. 10, it can be seen that in a preferred application or method of use, two mandible support devices 1000 are applied to the user, with one located on or about each side of the mandible. In FIG. 10, it can be seen again that the structural member 1010 of the mandible support device 1000 is sized to span the distance from the region of the zygomatic bone or maxilla to the region on, behind, or beneath the gonial angle. Specifically, as depicted in FIG. 10, the first end 1020 of the structural member 1010 is adhered to the epidermis covering the zygomatic bone and/or maxilla and the second end 1030 of the structural member 1010 is adhered to the epidermis covering or about the region on, beneath, or behind the gonial angle. In the embodiment shown in FIG. 10, the mandible support device 1000 includes a positioning component 1040. The positioning component is used to align the second end 1030 of the structural member 1010 to the gonial angle. The positioning component 1040 also provides additional passive support to restrict posterior movement of the mandible.

The support component of the structural member 1010 can be made of any flexible material upon which the adhesive component can be disposed. Such flexible material may have an elastic quality along all or part of its length, but such an elastic quality is not a requirement of the present invention. Because the structural member 1010 is intended to be applied to the epidermis of the head, face and/or neck of a human for use during sleep, the adhesive component of the structural member 1010 should allow for easy removal from the epidermis, while still being able to maintain its position on the epidermis for a period of at least eight to twelve hours. Similarly, because the structural member 1010 is intended to be applied to the epidermis of the head, face and/or neck of a human, and because the structural member 1010 is intended to remain in place for periods of time up to or exceeding twelve hours, ideally the material of which the support component of the structural member 1010 is made will allow for the transmission of moisture and/or air. This "breathability" of the support component of the structural member 1010 is intended to serve to increase the comfort of the mandible support device to the user.

The support component of the structural member 1010 may include a section that demonstrates elastic properties, or may be constructed entirely of a material that demonstrates elastic properties. Alternatively, the support component of the structural member 1010 may comprise an inelastic material. Where the support component of the structural member 1010 comprises a material that is partially or substantially elastic along its length, the elasticity should not be so great as to eliminate the substantial passive support of the mandible that is necessary for the proper functioning of the mandible support device 1000.

The mandible support device 1000 serves to provide passive support of the mandible, overcoming, at least in part, the reduction in muscular support that occurs as a result of the relaxation of muscles of the face and neck during sleep. The support component of the structural member 1010 of the mandible support device 1000 is anchored to the soft tissue of the region over or about the zygomatic bone and/or maxilla by contacting the adhesive component on one side of the first end 1020 of the support component of the structural member 1010 to the epidermis in the region of the zygomatic bone and/or maxilla, thereby adhering the first end 1020 of the structural member 1010 to the epidermis in the region of the zygomatic bone and/or maxilla. The second end 1030 of the structural member 1010 is then adhered to the skin covering the region immediately posterior to the gonial angle.

One of skill in the art would understand that the application positioning of the first end 1020 of the structural member 1010 can vary from user to user, or can vary about the face of the user while still performing the function of the invention. For example, depending on the material used for the structural member 1010, the adhesive material, and the geometry of a user's face, it may be determined that the optimal position of the first end 1020 of the structural member 1010 may be somewhat anterior to the zygomatic bone of the user, rotated in the direction of the user's nose.

A positioning component 1040 can be used to aid in the positioning of the second end 1030 of the structural member 1010 to the region on, behind, or beneath the gonial angle. The positioning component 1040 should be disposed on the structural member 1010 in such a manner that the location of the contours of the positioning component 1040 can be felt relative to the gonial angle when the structural member 1010 is applied on the user. The positioning component 1040 should be sufficiently flexible to be comfortable on the user's epidermis and to be able to conform to the shape and size of the region on, beneath, or behind the gonial angle. The positioning component 1040 should also be sufficiently rigid to provide some tactile resistance, thus providing tactile feedback to the user regarding placement of the second end 1030 of the structural member 1010 relative to the gonial angle.

The positioning component 1040 has an additional function of providing support to the mandible and reducing a shift of the mandible in a posterior direction. Specifically, the positioning component 1040 when adhered to the epidermis covering the head, face or neck on, behind or beneath the gonial angle provides a ledge-like structure against which the gonial angle can rest upon relaxation of the facial and neck muscles, thereby aiding in the prevention of a posterior shift of the mandible.

Returning to FIG. 8, in an alternative embodiment, one or more rib members 850 can be embedded within or otherwise disposed on the structural member 810 of the mandible support device 800. The rib member 850 may comprise one or more strips of rigid or semi-rigid material. Rib member 850 may comprise metal, plastic, or any other suitable material as would be understood by a person of skill in this art to perform the necessary function. The rib member 850 would provide support for the shape of the structural member 810 in a longitudinal direction, from the first end 820 to the second end 830, allowing the structural member 810 to maintain a shape approximating the shape of a human neck and face over the span from the region above the mandible to the region on, behind, or beneath the gonial angle. The shape of the rib member 850 may be fashioned such that when applied to the epidermis of the neck and face, the rib member 850 provides a force inward to the face and neck to bring the positioning component 840 in closer alignment with the gonial angle. The inward force immediately posterior to the gonial angle can provide additional support for the mandible by allowing the positioning component 840 to more effectively resist movement of the mandible in the posterior direction along the longitudinal axis of the structural member 810. The rib member 850 may also be configured to pass between the positioning component 840 and the structural member 810, as indicated at region 860. However, such a configuration is only one of several configurations that would be understood by a person of skill in the art.

One method of application of the mandible support device 800 to the face of the user begins with the application of the second end 830 to the skin in the region on, beneath, or behind the gonial angle, using the adhesive component that is disposed on the one side of the support component of the structural member 810. If the mandible support device 800 has a positioning component 840, the positioning component 840 should be positioned directly on, beneath, or behind the gonial angle, such that the curve of the positioning component 840 approximates the gonial angle. If the mandible support device 800 includes one or more semi-rigid members 850, the end of the structural member 810 should be affixed to the epidermis on, behind, or beneath the gonial angle such that positioning component 840, if present, is allowed to press slightly inward at its location beneath or behind the gonial angle. If no positioning component 840 is present on the structural member 810, the second end 830 of the structural member 810 should be placed sufficiently beyond the gonial angle so that the structural member 810 can provide resistance against posterior movement of the mandible. In this method of use of the mandible support device 800, the first end 820 of the structural member 810 is pulled toward the zygomatic bone and/or maxilla and adhered to the epidermis covering the area of the zygomatic bone and/or maxilla using the adhesive component that is disposed on one side of the support component of the structural member 810. The force with which the first end 820 of the support component of the structural member 810 is pulled beneath or behind the gonial angle and toward the zygomatic bone and/or maxilla will affect the amount of support provided to the mandible. The degree of support provided can therefore be altered depending on the needs of the user, where a greater amount of support can be provided for users that experience a higher degree of posterior mandibular movement during sleep. Certainly, application of the mandible support device 800 to the user can be accomplished by adhering the first end 820 of the structural member 810 to the region of the zygomatic bone first, followed by pulling the second end 830 of the structural member 810 toward the gonial angle and adhering the second end 830 of the structural member 810 to the epidermis covering the region of the face and neck on, beneath, or behind the gonial angle. However, because the positioning of the second end 830 of the structural member 810 is of primary importance to the most effective application of the mandible support device 800, the preferred method of use entails first adhering the second end 830 of the structural member 810 to the soft tissues covering the region on, behind, or beneath the gonial angle.

Other and further embodiments utilizing one or more aspects of the inventions described above can be devised without departing from the spirit of Applicant's invention. Further, the various methods and embodiments of the mandible support device can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A method of restricting posterior movement of the mandible in a human, comprising:
   providing a pair of mandibular support devices, each device having a length between a first end and a second end not exceeding a distance between a region of a zygomatic bone and a region on, beneath, or behind a gonial angle, and comprising a structural member that is elastic along at least a portion of its length, the structural member comprising a support component and an adhesive component; the support component comprising a first section and a second section; the adhesive component disposed on a surface of the first section and the second section;
   applying a first mandibular support device of the pair of mandibular support devices to one side of the human face such that the first section of the support component engages epidermis on the zygomatic bone using the adhesive component of the structural member;
   applying the second section of the support component of the first device to the epidermis covering the mandible about the region of the gonial angle using the adhesive component of the structural member;
   stretching the first mandibular support device to create a tensile force in the first mandibular support device sufficient to restrict posterior movement of the mandible that normally occurs as a result of gravity and muscle relaxation while allowing intentional movement of the mandible; and
   applying the second mandibular support device of the pair of mandibular support devices to another side of the human face in substantially identical manner.

2. The method of claim 1, further comprising:
   reducing restriction of air flow in the throat.

3. The method of claim 2, wherein reducing the restriction of air flow comprises reducing sagging of soft tissue in a back of the throat to a degree sufficient to reduce snoring.

4. The method of claim 1, further comprising:
   increasing air flow through the throat.

5. The method of claim 4, wherein increasing air flow comprises reducing sagging of soft tissue in a back of the throat to a degree sufficient to reduce snoring.

6. The method of claim 1, wherein the structural member is breathable.

7. The method of claim 6, wherein affixing the first and second sections provide sufficient tensile force to passively support weight of the mandible while allowing intentional movement of the mandible.

8. The method of claim 1, wherein each support component further comprises a positioning component that is at least partially flexible and is disposed about the second section of the support component; and further comprising:

aligning the positioning component to the gonial angle of the patient.

9. The method of claim 1, wherein the second sections are applied on, behind or beneath the gonial angles.

10. The method of claim 1, wherein the pair of devices provides passive external support of the mandible.

11. The method of claim 1, wherein applying the pair of devices provides sufficient tensile force to passively support weight of the mandible while allowing intentional movement of the mandible.

12. A method of treating snoring, comprising:
providing a mandibular support device having a length between a first end and a second end not exceeding a distance between a region of a zygomatic bone and a region on, beneath, or behind a gonial angle, said mandibular support device including a structural member comprising a support component and an adhesive component; said support component comprising a first section and a second section; at least a portion of the support component is substantially flexible; wherein the adhesive component is disposed on one side of the structural member; and wherein the entirety of the length of the mandibular support device extends between the first and second ends and the mandibular support device is elastic along at least a portion of its length; and
temporarily adhering the first section of the support component to epidermis over the zygomatic bone using the adhesive component of the structural member, and temporarily affixing the second section of the support component to the epidermis about the region on, beneath, or behind the gonial angle using the adhesive component of the structural member so that tension sufficient to restrict posterior movement of the mandible while allowing intentional movement of the mandible is applied between the first section and the second section of the support component.

13. The method of claim 12, further comprising:
creating sufficient tension between the first section of the support component and the second section of the support component to reduce restriction of air flow in the throat.

14. The method of claim 13, further comprising:
reducing sagging of soft tissue in a back of the throat to a degree sufficient to reduce snoring during sleep.

15. The method of claim 12, further comprising:
the support component further comprising a positioning component disposed about the second section of the support component, wherein said positioning component is at least partially flexible; and
locating the positioning component about or behind the gonial angle on which to temporarily affix the second section of the support component by substantially aligning the positioning component to the gonial angle.

16. The method of claim 12, wherein affixing the first and second sections provides passive external support of the mandible.

17. The method of claim 12, wherein the structural member is breathable.

18. A method of supporting a human mandible, comprising:
providing a pair of mandibular support devices each having a length between a first end and a second end not exceeding a distance between a region of a zygomatic bone and a region on, beneath, or behind a gonial angle, and each comprising a body that is stretchable along at least a portion of its length and comprising a first section and a second section, and wherein the first and second sections have an adhesive disposed thereon;
adhering a first of the pair of devices to one side of the human face such that the first section adheres to epidermis covering at least a portion of the zygomatic bone;
stretching the first of the pair of devices to create a tensile force within the first device;
adhering the second section of the first of the pair of devices such that it adheres to epidermis on or about the region on, beneath or behind the gonial angle;
adhering the second of the pair of devices to the other side of the human face in substantially identical manner; and
wherein the pair of devices applied to the human face create sufficient tensile force to support the weight of the mandible during sleep and reduce posterior movement of the mandible while allowing intentional movement of the mandible.

19. The method of claim 18, wherein the body is breathable.

20. A method of supporting a human mandible, comprising:
providing a first mandibular support device having a length extending between a first end and a second end not exceeding a distance between a region of a zygomatic bone and a region on, beneath, or behind a gonial angle, the first support device comprising a breathable material and having an adhesive component disposed adjacent at least the first end and the second end and configured to temporarily adhere the support device to epidermis;
adhering to a first side of the human face the first end of the first support device to epidermis covering the zygomatic bone using a portion of the adhesive component;
elastically stretching the first support device to create a tensile force within the first support device between the first and second ends;
adhering to the first side of the human face the second end of the first support device to epidermis about the region on, beneath or behind the gonial angle using another portion of the adhesive component;
and applying the force generated between the first and second ends of the first support device to reduce posterior movement of the mandible while allowing intentional movement of the mandible.

* * * * *